(12) United States Patent
Ding et al.

(10) Patent No.: US 7,774,978 B2
(45) Date of Patent: Aug. 17, 2010

(54) METHOD OF CONTROLLING THE RELEASE OF AGRICULTURAL ACTIVE INGREDIENTS FROM TREATED PLANT SEEDS

(75) Inventors: Yiwei Ding, Ballwin, MO (US); Jawed Asrar, Chesterfield, MO (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 11/832,397

(22) Filed: Aug. 1, 2007

(65) Prior Publication Data

US 2008/0004178 A1 Jan. 3, 2008

Related U.S. Application Data

(63) Continuation of application No. 11/109,131, filed on Apr. 19, 2005, now abandoned, which is a continuation of application No. 10/079,000, filed on Feb. 18, 2002, now abandoned.

(60) Provisional application No. 60/277,503, filed on Mar. 21, 2001.

(51) Int. Cl.
*A01C 1/06* (2006.01)
*A01G 5/06* (2006.01)
*A01N 25/26* (2006.01)

(52) U.S. Cl. ............... 47/57.6; 427/4; 504/100
(58) Field of Classification Search ............ 427/4; 47/57.6; 504/100
See application file for complete search history.

(56) References Cited

U.S. PATENT DOCUMENTS

| | | | |
|---|---|---|---|
| 3,703,404 A | 11/1972 | Kirk | |
| 3,911,183 A | 10/1975 | Hinkes | |
| 4,245,432 A | 1/1981 | Dannelly | |
| 4,251,952 A | 2/1981 | Porter et al. | |
| 4,272,276 A | 6/1981 | Szejtli et al. | |
| 4,272,417 A | 6/1981 | Barke et al. | |
| 4,337,330 A | 6/1982 | Robeson | |
| 4,729,190 A * | 3/1988 | Lee | 47/57.6 |
| 4,735,015 A | 4/1988 | Schmolka | |

(Continued)

FOREIGN PATENT DOCUMENTS

GB 2110518 4/1982

(Continued)

OTHER PUBLICATIONS

International Search Report for International Application No. PCT/US02/04699 dated Mar. 9, 2002.

(Continued)

*Primary Examiner*—Timothy H Meeks
*Assistant Examiner*—Mandy C Louie
(74) *Attorney, Agent, or Firm*—McAndrews, Held & Malloy, Ltd.

(57) ABSTRACT

A method of controlling the release rate of an agricultural active ingredient from a seed that has been treated with that active includes providing a seed that has been treated with the active ingredient, applying to the treated seed a film that includes an emulsion of a polymer in a liquid in which both the agricultural active ingredient and the polymer have low levels of solubility, and then curing the film to form a water insoluble polymer coating on the surface of the treated seed. Seeds that have been treated by this method are also provided.

9 Claims, 2 Drawing Sheets

U.S. PATENT DOCUMENTS

| | | | |
|---|---|---|---|
| 4,735,017 A * | 4/1988 | Gago et al. | 47/57.6 |
| 4,759,956 A * | 7/1988 | Amer et al. | 427/213 |
| 4,802,305 A | 2/1989 | Kojimoto et al. | |
| 4,808,430 A | 2/1989 | Kouno | |
| 5,129,180 A * | 7/1992 | Stewart | 47/57.6 |
| 5,435,821 A | 7/1995 | Duvdevani et al. | |
| 5,849,320 A | 12/1998 | Turnblad et al. | |
| 5,876,739 A | 3/1999 | Turnblad et al. | |
| 5,969,032 A * | 10/1999 | Phan et al. | 524/460 |
| 6,329,319 B1 * | 12/2001 | Puglisi et al. | 504/100 |
| 6,858,634 B2 | 2/2005 | Asrar et al. | |
| 2002/0134012 A1 | 9/2002 | Ding et al. | |
| 2002/0177526 A1 | 11/2002 | Chen et al. | |

FOREIGN PATENT DOCUMENTS

| | | |
|---|---|---|
| WO | 93/25078 | 12/1993 |
| WO | 98/32726 | 7/1998 |
| WO | 98/32773 | 7/1998 |
| WO | 99/00013 | 1/1999 |
| WO | 99/57959 | 11/1999 |
| WO | 00/05950 | 2/2000 |
| WO | 00/06611 | 2/2000 |
| WO | 00/06612 | 2/2000 |
| WO | 02/15703 | 2/2002 |

OTHER PUBLICATIONS

Tsuda, M., et al.; "Simeconazole (F-155), a Novel Systemic Fungicide with Broad-Spectrum Activiity for Seed Treatment," presented at the BCPC Conference—Pests & Diseases 2000, pp. 557-562.

Stepan Company presentation entitled NMS Latex for Agricultural Formulations, Mar. 2000, pp. 1-14.

Abstract XP-002210612 of RU 2142215 (Yunosov), Oct. 12, 1999.

Anonymous; undated; Luvitec advertisement; pp. 3-9 (downloaded from Internet).

Anonymous; undated; Insecticide Market Trends and Potential Water Quality Implications; pp. 23-27, 35, 79, 80 (downloaded from Internet).

Anonymous; undated; Material Safety Data Sheet; 7 pages (downloaded from Internet).

* cited by examiner

METHOD OF CONTROLLING THE RELEASE OF AGRICULTURAL ACTIVE INGREDIENTS FROM TREATED PLANT SEEDS

The present application claims the benefit of U.S. Provisional Application Ser. No. 60/277,503 filed Mar. 21, 2001, which is incorporated herein by reference thereto.

BACKGROUND OF THE INVENTION

1. Field of the Invention

The present invention relates to methods for controlling the release of agricultural active ingredients from treated plant seeds, and more particularly to methods for controlling the release of agricultural active ingredients from treated plant seeds by the use of seed coatings.

2. Description of Related Art

The development and use of pesticides has increased the yield of most agronomically important plants. Pesticides, including herbicides, insecticides, nematocides, acaracides, fungicides, bactericides, and the like, are now widely applied to soils prior to, during, or after seed planting, or are applied directly or indirectly to growing plants at various times during the growing season.

Widespread use of pesticides has not been without problems, however, due to the wide spectrum of activity and high toxicity of some pesticides. Such negative results have been exacerbated by the widespread distribution of pesticides in the environment through such vectors as runoff, wind-drift, leaching, animal activity and the like. This type of movement of pesticides away their point of application and target of activity also requires that higher levels of the pesticide be used in order to insure that the application provides the desired pesticidal activity for the desired period of time that it is required.

One method that has been found to be promising in some applications is the treatment of plant seeds with pesticides. General information on this subject is provided in, for example, Chemtech, 8.284-287 (May 1978). In situations where seed treatment is effective, it can reduce the amount of pesticide that is required to obtain a desired level of activity. Other advantages of direct, pre-planting seed treatment include reducing the number of separate field passes that a farmer must make to prepare for, plant, and raise a crop, and limiting at least the initial zone of pesticidal activity to the seed and its immediate environment. Further information about seed coatings has been published by Barke et al., who describe seed coating compositions comprising a stabilizing polyol in U.S. Pat. No. 4,272,417. Seed coatings containing polyelectrolyte complexes are disclosed by Dannelly in U.S. Pat. No. 4,245,432. Kouno has described a method of applying gel coating to seeds in U.S. Pat. No. 4,808,430. In U.S. Pat. No. 4,735,015, Schmolka has described enveloping a seed in a coating containing certain polyoxyethylene-polyoxybutylene block copolymers.

Early seed treatment applications were often carried out by simply applying a pesticide—a fungicide, for example—directly to a seed, followed by drying the treated seed for storage and use. It was soon apparent, however, that this technique also had drawbacks, such as toxicity of the pesticide to the seed, high rates of loss of the pesticide during storage and the exposure of workers handling and planting the seed to high levels of the pesticide. In cases where the pesticide was water soluble or easily leached from the seed, the loss of pesticide from the zone of the seed could be rapid. Not only could this reduce the efficacy of the treatment, but could also cause unwanted release of the pesticide into the environment.

In many cases, it is desirable to retard or control the release of the active from the seed because of safety considerations and to increase the efficiency of use of the active. For example, if release of a pesticide can be controlled so that the concentration of the pesticide in the zone of the seed reaches and remains at an effective level during the time the target pest is active, the efficiency of use of the pesticide is increased over what would ordinarily be expected if the pesticide was merely applied to the soil at planting. Examples of methods to control the release of actives by the use of seed coatings have been described by, among others, Turnblad et al. in U.S. Pat. Nos. 5,849,320 and 5,876,739, who disclosed insecticidal coatings comprising a polymer binder, an insecticide and a filler, where the binder formed a matrix for the insecticide and the filler. Application of such a coating to a seed and the optional subsequent application of a protective polymer overcoating were also described.

One of the considerations of including a pesticide, such as an insecticide, in the seed coating itself is that the active agent is present throughout the coating and even on the outer surface of the coated seed. This permits anyone handling the seed to contact the active ingredient directly. In order to minimize this contact, it is necessary to add a second, additional, coating to the seed. This requires additional materials and results in higher cost of seed preparation.

Another problem that has hindered the development of seed coatings that control the release of pesticides has been the requirement for coatings that are carefully tailored to provide a certain chemical relationship with the pesticide. For example, the combination of the pesticide and the coating must meet certain criteria of release rate, protection of the active, protection of the seed, and the like, while not binding the pesticide so tightly that release is prevented entirely. The development of coating formulations that meet these criteria has routinely taken significant time and effort, and the formulations are most often limited to use with one type of pesticide.

Accordingly, it would be useful to devise a method for controlling the release of agricultural actives from a seed that has been treated with such actives where the methods are easy, fast and economical to administer, and are effective in controlling the release of the active from the treated seed. Moreover, it would be useful if such methods could be used with a wide range of agricultural actives and if they could be practiced without the inconvenience and expense of having to develop a polymer coating having certain chemical compatibility between a particular active and the polymer.

SUMMARY OF THE INVENTION

Briefly, therefore, the present invention is directed to a novel method of controlling the release rate of an agricultural active ingredient from a seed treated with the active ingredient, the method comprising the steps of: providing a seed that has been treated with an agricultural active ingredient; applying to the treated seed a film comprising an emulsion of a polymer in a liquid in which both the agricultural active ingredient and the polymer have low levels of solubility; and curing the film to form a water insoluble polymer coating on the surface of the treated seed.

The present invention is also directed to a novel treated seed that is coated by the method described above.

The present invention is also direct to a novel method of protection of a seed comprising treating the seed by the method described above.

Among the several advantages found to be achieved by the present invention, therefore, may be noted the provision of a method of controlling the release rate of an agricultural active ingredient from a seed treated with the active ingredient, where the method is easy, fast and economical to administer; the provision of such a method that is effective in controlling the release of the active from the treated seed; the provision of such a method that can be used with a wide range of agricultural actives; and the provision of such a method that can be practiced without the inconvenience and expense of having to develop a polymer coating having certain chemical compatibility between a particular active and the polymer.

DETAILED DESCRIPTION OF THE INVENTION

In accordance with the present invention, it has been discovered that the release rate of an agricultural active ingredient from a seed that has been treated with such active can be controlled by applying to the treated seed a film of an emulsion of a polymer in a liquid in which both the agricultural active ingredient and the polymer have low levels of solubility, and then curing the film to form a water insoluble polymer coating on the surface of the treated seed.

This method has been found to be an effective way to provide seeds that have been treated with, for example, a pesticide, that have a controlled release rate of the pesticide into the environment around the planted seed, thereby increasing the efficiency of the pesticide. Moreover, the polymer coating is easy and economical to apply to the seeds, and the application can be done in the same equipment in which the seeds are treated with pesticide. Unlike conventional methods of forming controlled release compositions, the novel method provides the unexpected advantage that the polymer that is used to form the coating does not necessarily have to have any particular chemical compatibility with the active ingredient. Therefore, the method is believed to be especially useful for seeds that have been treated with two or more active ingredients that have chemical characteristics that are significantly different from each other. Such a combination of actives would normally make it difficult, if not impossible, to design a typical controlled-release formulation having desirable release characteristics for both active ingredients.

It is believed that another surprising property of the novel method is that it results in treated seed having a single coating that has very low levels of the active ingredient at the outer surface of the coating. This is thought to remove the need for the application of a separate overcoating of the seed, while providing a treated seed that is safer to handle and provides greater control of the active than an uncoated seed.

Polymers that can be used to form the present coating are those that are capable of forming a water insoluble coating upon curing. When it is said that the coating is a water insoluble, it is meant is that the coating has a water solubility of less than about 1%, and preferably less than about 0.1%, by weight, at 25° C. Among the advantages that a coating having low water solubility provides is that the loss of the coating due to water solubilization in the environment is reduced. It is also preferred that the polymer is one that is non-toxic to the seed to which it is to be applied, i.e., that it is non-phytotoxic.

Polymers that are suitable for use in the present method can be polyesters, polycarbonates, co-polymers of styrene, and mixtures thereof. Examples of preferred polymers are acrylonitrile-butadiene-styrene terpolymer (ABS); ABS modified polyvinylchloride; ABS-polycarbonate blends; acrylic resins and co-polymers: poly(methacrylate), poly(ethylmethacrylate), poly(methylmethacrylate), methylmethacrylate or ethylmethacrylate copolymers with other unsaturated monomers; casein; cellulosic polymers: ethyl cellulose, cellulose acetate, cellulose acetatebutyrate; ethylene vinyl acetate polymers and copolymers; poly(ethylene glycol); poly(vinylpyrrolidone); acetylated mono-, di-, and tri-glycerides; poly(phosphazene); chlorinated natural rubber; polybutadiene; polyurethane; vinylidene chloride polymers and copolymers; styrene-butadiene copolymers; styrene-acrylic copolymers; alkylvinylether polymers and copolymers; cellulose acetate phthalates; epoxies; ethylene copolymers: ethylene-vinyl acetate-methacrylic acid, ethylene-acrylic acid copolymers; methylpentene polymers; modified phenylene oxides; polyamides; melamine formaldehydes; phenolformaldehydes; phenolic resins; poly(orthoesters); poly(cyanoacrylates); polydioxanone; polycarbonates; polyesters; polystyrene; polystyrene copolymers: poly(styrene-co maleic anhydride); urea-formaldehyde; urethanes; vinyl resins: vinyl chloride-vinyl acetate copolymers, polyvinyl chloride and mixtures of two or more of these.

The polymers derived from unsaturated amine salts that are described in WO 98/32726, WO 98/32773, WO 00/05950, WO 00/06612, and WO 00/06611, to the Stepan Company, are preferred. More preferred are the polymers that are known commercially as NMS Latex polymers (Stepan Company).

Polymers that are biodegradable are also useful in the present invention. As used herein, a polymer is biodegradable if is not water soluble, but is degraded over a period of several weeks when placed in an application environment. Examples of biodegradable polymers that are useful in the present method include biodegradable polyesters; starch-polyester alloys; starch; starch-PCL blends; polylactic acid (PLA)-starch blends; polylactic acid; poly(lactic acid-glycolic acid) copolymers; PCL; cellulose esters; cellulose acetate butyrate; starch esters; starch ester-aliphatic polyester blends; modified corn starch; polycaprolactone; poly(n-amylmethacrylate); ethyl cellulose; wood rosin; polyanhydrides; polyvinylalcohol (PVOH); polyhydroxybutyrate-valerate (PHBV); biodegradable aliphatic polyesters; and polyhydroxybutyrate (PHB). A biodegradable aliphatic polyester such as BIONOLLE, from Showa High Polymer, Tokyo, Japan, is preferred.

The polymer emulsion of the present method can also include a non-migrating surfactant. When it is said that the surfactant is "non-migrating", it is meant that the surfactant is substantially insoluble in water and, if the liquid used to form the polymer emulsion is other than water, then the surfactant is also substantially insoluble in that liquid. When it is said that the surfactant is "substantially insoluble", it is meant that it has a solubility in a particular liquid at 25° C. of less than about 1% by weight, preferably of less than about 0.1% by weight, and more preferably of less than about 0.01% by weight.

The non-migrating surfactant can also be a molecule that is bound to the polymer that is described above, rather than being a separate entity. Such binding can be in the nature of a chemical bond, or it can be in the nature of an ionic attraction.

Non-migrating surfactants that are useful in the present method are disclosed by Guyot, A., in *Current Opinions in Colloid and Surface Science, pp.* 580-585 (1996); Guyot, A. et al., in *Advances in Polymer Science,* 11, 43-65, Springer-Verlag, Berlin (1994); and by Holmberg, K., in *Progress in Organic Coatings,* 20.325-337 (1992). Preferred non-migrating surfactants are described in WO 00/05950, and include diallyl amine pluronics (available from BASF), linoleic alcohol derivatives (available from ICI), allyl alkyl phenol derivatives (available from DKS, Japan), acrylate derivatives (available from PPG), allyl alcohol alkenyl succinic anhydride derivatives (available from KAO, Japan), Polystep RA series (maleic derivatives, available from Stepan Co.), maleic derivatives (available from Rhone Poulenc), and Trem LF-40 allyl sulfosuccinate derivatives (available from Henkel).

It is believed that the use of a surfactant having the characteristics described above provides the benefits of (1) permitting control of permeability of the coating, which modulates the release rate of the active through the coating and also controls the rate of water permeation from the soil into the seed; and (2) remaining with the polymer while in liquid emulsion form; and (3) the surfactant is not lost from the coating by contact with water after planting. The coating permeability is related to the glass transition temperature of the polymer/surfactant mix ($T_g$,), and this parameter can be used as an indicator of the degree of permeability of the coating.

In a preferred embodiment of the invention, the water insoluble polymer and the non-migrating surfactant and the relative amounts of each are selected so that the polymer coating that is formed from the water insoluble polymer and the non-migrating surfactant has a glass transition temperature within a pre-selected range, thereby providing a coating which retards the release rate of the agricultural active ingredient from the seed by a desired amount. The glass transition temperature of the polymer coating can be within the range of from about −5° C. to about 75° C. It is preferred, however that the glass transition temperature of the polymer coating is within the range of from about 10° C. to about 50° C., more preferred that the glass transition temperature of the polymer coating is within the range of from about 15° C. to about 40° C., and even more preferred that the glass transition temperature of the polymer coating is within the range of from about 15° C. to about 25° C.

It is believed that the subject method can be used on the seed of any plant. However, it is preferably used on seeds of plant species that are agronomically important. In particular, the seeds can be of corn, peanut, canola/rapeseed, soybean, curcubits, cotton, rice, sorghum, sugar beet, wheat, barley, rye, sunflower, tomato, sugarcane, tobacco, oats, was well as other vegetable and leaf crops. It is preferred that the seed be corn, soybeans, or cotton seed, and more preferred that the seed be corn.

Seeds on which the present invention can be used can be seeds that do not have a transgenic event, or can be transgenic seeds.

Although the present method can be applied to a seed at any state of development, it is preferred that the method is applied after the seed has been harvested and before the seed has been planted. It is also preferred that the subject method be applied to a seed that has been dried to a moisture level that is suitable for stable storage.

The subject method can be used to control the release of almost any type of agricultural active ingredient that has been applied to a seed. For example, the active can be a growth factor, a growth regulator, a pesticide, or the like. If the active is a pesticide, such pesticide can be selected from herbicides, molluscicides, insecticides, nematocides, acaricides, fungicides, bactericides, and the like. Although the subject method can be used for seeds that have been treated with only one active, it is also useful for seeds that have been treated by two or more active ingredients.

Pesticides suitable for use in the invention include pyrethrins and synthetic pyrethroids; azoles, oxadizine derivatives; chloronicotinyls; nitroguanidine derivatives; triazoles; organophosphates; pyrrols; pyrazoles; phenyl pyrazoles; diacylhydrazines; biological/fermentation products; and carbamates. Known pesticides within these categories are listed in *The Pesticide Manual,* 11th Ed., C. D. S. Tomlin, Ed., British Crop Protection Council, Farnham, Surry, UK (1997).

Pyrethroids that are useful in the present composition include pyrethrins and synthetic pyrethroids. The pyrethrins that are preferred for use in the present method include, without limitation, 2-allyl-4-hydroxy-3-methyl-2-cyclopenten-1-one ester of 2,2-dimethyl-3-(2-methylpropenyl)-cyclopropane carboxylic acid, and/or (2-methyl-1-propenyl)-2-methoxy-4-oxo-3-(2-propenyl)-2-cyclopenten-1-yl ester and mixtures of cis and trans isomers thereof (Chemical Abstracts Service Registry Number ("CAS RN") 8003-34-7).

Synthetic pyrethroids that are preferred for use in the present invention include (s)-cyano(3-phenoxyphenyl)methyl-4-chloro alpha (1-methylethyl)benzeneacetate (fenvalerate, CAS RN 51630-58-1), (S)-cyano-(3-phenoxyphenyl) methyl (S)-4-chloro-alpha-(1-methylethyl)benzeneacetate (esfenvalerate, CAS RN 66230-04-4), (3-phenoxyphenyl)-methyl(+)cis-trans-3-(2,2-dichoroethenyl)-2,2-dimethylcyclopropanecarboxylate (permethrin, CAS RN 52645-53-1), (±) alpha-cyano-(3-phenoxyphenyl)methyl(+)-cis,trans-3-(2,2-dichloroethenyl)-2,2-dimethyl-cyclopropane carboxylate (cypermethrin, CAS RN 52315-07-8), (beta-cypermethrin, CAS RN 65731-84-2), (theta cypermethrin, CAS RN 71697-59-1), S-cyano(3-phenoxyphenyl)methyl(±)cis/trans 3-(2,2-dichloroethenyl) 2,2 dimethylcyclopropane carboxylate (zeta-cypermethrin, CAS RN 52315-07-8), (s)-alpha-cyano-3-phenoxybenzyl(1R,3R)-3-(2,2-dibromovinyl)-2,2-dimethylcyclopropanecarboxylate (deltamethrin, CAS RN 52918-63-5), alpha-cyano-3-phenoxybenzyl 2,2,3,3,-tetramethyl cyclopropoanecarboxylate (fenpropathrin, CAS RN 64257-84-7), (RS)-alpha-cyano-3-phenoxybenzyl(R)-2-[2-chloro-4-(trifluoromethyl)anilino]-3-methylbutanoate (tau-fluvalinate, CAS RN 102851-06-9), (2,3,5,6-tetrafluoro-4-methylphenyl)methyl-(1-alpha, 3-alpha)-(Z)-(±)-3-(2-chloro-3,3,3-trifluoro-1-propenyl)-2,2-dimethylcyclopropanecarboxylate (tefluthrin, CAS RN 79538-32-2), (±)-cyano(3-phenoxyphenyl)methyl(±)-4-(difluoromethoxy)-alpha-(1-methylethyl)benzeneacetate (flucythrinate, CAS RN 70124-77-5), cyano(4-fluoro-3-phenoxyphenyl)methyl 3-[2-chloro-2-(4-chlorophenyl)ethenyl]-2,2-dimethylcyclopropanecarboxylate (flumethrin, CAS RN 69770-45-2), cyano(4-fluoro-3-phenoxyphenyl)methyl 3-(2,2-dichloroethenyl)-2,2-dimethyl-cyclopropanedarboxylate (cyfluthrin, CAS RN 68359-37-5), (beta cyfluthrin, CAS RN 68359-37-5), (transfluthrin, CAS RN 118712-89-3), (S)-alpha-cyano-3-phenoxybenzyl(Z)-(1R-cis)-2,2-dimethyl-3-[2-(2,2,2-trifluoro-trifluoromethyl-ethoxycarbonyl)vinyl]cyclopropane carboxylate (acrinathrin, CAS RN 101007-06-1), (1R cis) S and (1S cis) R enantiomer isomer pair of alpha-cyano-3-phenoxybenzyl-3-(2,2-dichlorovinyl)-2,2-dimethylcyclopropane carboxylate (alpha-cypermethrin, CAS RN 67375-30-8), [1R,3S)3(1'RS)(1',2',2',2'-tetrabromoethyl)]-2,2-dimethylcyclopropanecarboxylic acid (s)-alpha-cyano-3-phenoxybenzyl ester (tralomethrin, CAS RN 66841-25-6), cyano-(3-phenoxyphenyl)methyl 2,2-dichloro-1-(4-ethoxyphenyl)cyclopropane carboxylate (cycloprothrin, CAS RN 63935-38-6), [1α,3α(Z)]-(±)-cyano-(3-phenoxyphenyl)methyl 3-(2-chloro-3,3,3-trifluoro-1-propenyl)-2,2-dimethylcyclopropanecarboxylate (cyhalothrin, CAS RN 68085-85-8), [1-alpha (s), 3-alpha(z)]-cyano(3-phenoxyphenyl)methyl-3-(2-chloro-3,3,3-trifluoro-1-propenyl)-2,2-dimethylcyclopropanecarboxylate (lambda cyhalothrin, CAS RN 91465-08-6), (2-methyl-[1,1'-biphenyl]-3-yl)methyl-3-(2-chloro-3,3,3-trifluoro-1-propenyl)-2,2-dimethylcyclopropanecarboxylate (bifenthrin, CAS RN 82657-04-3), 5-1-benzyl-3-furylmethyl-d-cis(1R,3S,E)2,2-dimethyl-3-(2-oxo,-2,2,4,5 tetrahydro thiophenylidenemethyl)cyclopropanecarboxylate (kadethrin, RU15525, CAS RN 58769-20-3), [5-(phenylmethyl)-3-furanyl]-3-furanyl-2,2-dimethyl-3-(2-methyl-1-propenyl)cyclopropane carboxylate (resmethrin, CAS RN 10453-86-8), (1R-trans)-[5-(phenylmethyl)-3-furanyl]methyl 2,2-dimethyl-3-(2-methyl-1-propenyl)cyclopropanecarboxylate (bioresmethrin, CAS RN 28434-01-7), 3,4,5,6-tetrahydro-phthalim idomethyl-(1RS)-cis-trans-chrysanthemate (tetramethrin, CAS RN 7696-12-0), 3-phenoxybenzyl-d,l-cis,trans 2,2-dimethyl-3-(2-methyl-propenyl)cyclopropane carboxylate (phenothrin, CAS RN 26002-80-2); (empenthrin, CAS RN 54406-48-3); (cyphenothrin; CAS RN 39515-40-7), (prallethrin, CAS RN 23031-36-9), (imiprothrin, CAS RN 72963-72-5), (RS)-3-allyl-2-methyl-4-oxcyclopent-2-enyl-(1S,3R;1R,3S)-2,2-dimethyl-3-(2-methylprop-1-enyl)cyclopropanecarboxylate (allethrin, CAS RN 584-79-2), (bioallethrin, CAS RN 584-79-2), and (ZXI8901, CAS RN 160791-64-0). It is believed that mixtures of one or more of the aforementioned synthetic pyrethroids can also be used in the present invention. Particularly preferred synthetic pyrethroids are tefluthrin, lambda cyhalothrin, bifenthrin, permethrin and cyfluthrin. Even more preferred synthetic pyrethroids are tefluthrin and lambda cyhalothrin, and yet more preferred is tefluthrin.

Insecticides that are oxadiazine derivatives are useful in the subject method. The oxadizine derivatives that are preferred for use in the present invention are those that are identified in U.S. Pat. No. 5,852,012. More preferred oxadiazine derivatives are 5-(2-chloropyrid-5-ylmethyl)-3-methyl-4-nitroiminoperhydro-1,3,5-oxadiazine, 5-(2-chlorothiazol-5-ylmethyl)-3-methyl-4-nitroiminoperhydro-1,3,5-oxadiazine, 3-methyl-4-nitroimino-5-(1-oxido-3-pyridinomethyl)perhydro-1,3,5-oxadiazine, 5-(2-chloro-1-oxido-5-pyridiniomethyl)-3-methyl-4-nitroiminoperhydro-1,3,5-oxidiazine; and 3-methyl-5-(2-methylpyrid-5-ylmethyl)-4-nitroiminoperhydro-1,3,5-oxadiazine. Even more preferred is thiamethoxam (CAS RN 153719-23-4).

Chloronicotinyl insecticides are also useful in the subject method. Chloronicotinyls that are preferred for use in the subject composition are described in U.S. Pat. No. 5,952,358, and include acetamiprid ((E)-N-[(6-chloro-3-pyridinyl)methyl]-N'-cyano-N-methyleneimidamide, CAS RN 135410-20-7), imidacloprid (1-[(6-chloro-3-pyridinyl)methyl]-N-nitro-2-imidazolidinimime, CAS RN 138261-41-3), and nitenpyram (N-[(6-chloro-3-pyridinyl)methyl]-N-ethyl-N'-methyl-2-nitro-1,1-ethenediamine, CAS RN 120738-89-8).

Nitroguanidine insecticides are useful in the present method. Such nitroguanidines include those described in U.S. Pat. Nos. 5,633,375, 5,034,404 and 5,245,040, and, in particular, TI-435 (N-[(2-chloro-5-thiazoyl)methyl]-N'-methyl-N"-nitro,[C(E)]-(9Cl)-guanidine, (having a common name of clothianidin) CAS RN 210880-92-5).

Pyrrols, pyrazoles and phenyl pyrazoles that are useful in the present method include those that are described in U.S. Pat. No. 5,952,358. Preferred pyrazoles include chlorfenapyr (4-bromo-2-(4-chlorophenyl)-1-ethoxymethyl-5-trifluoromethylpyrrole-3-carbonitrile, CAS RN 122453-73-0), fenpyroximate ((E)-1,1-dimethylethyl-4[[[[(1,3-dimethyl-5-phenoxy-1H-pyrazole-4-yl)methylene]amino]oxy]methyl] benzoate, CAS RN 111812-58-9), and tebufenpyrad (4-chloro-N[[4-1,1-dimethylethyl)phenyl]methyl]-3-ethyl-1-methyl-1H-pyrazole-5-carboxamide, CAS RN 119168-77-3). A preferred phenyl pyrazole is fipronil (5-amino-[2,6-dichloro-4-(trifluoromethyl)phenyl]-4-[(1R,S)-(trifluoromethyl)sulfinyl]-1H-pyrazole-3-carbonitrile, CAS RN 120068-37-3).

Diacylhydrazines that are useful in the present invention include halofenozide (4-chlorobenzoate-2-benzoyl-2-(1,1-dimethylethyl)-hydrazide, CAS RN 112226-61-6), methoxyfenozide (RH-2485; N-tert-butyl-N'-(3-methoxy-o-toluoyl)-3,5-xylohydrazide, CAS RN 161050-58-4), and tebufenozide (3,5-dimethylbenzoic acid 1-(1,1-dimethylethyl)-2-(4-ethylbenzoyl)hydrazide, CAS RN 112410-23-8).

Triazoles, such as amitrole (CAS RN 61-82-5) and triazamate are useful in the method of the present invention. A preferred triazole is triazamate (ethyl-[[1-[(dimethylamino)carbonyl]-3-(1,1-dimethylethyl)-1H-1,2,4-triazol-5-yl]thio] acetate, CAS RN 112143-82-5).

Biological/fermentation products, such as avermectin (abamectin, CAS RN 71751-41-2) and spinosad (XDE-105, CAS RN 131929-60-7) are useful in the present method.

Organophosphate insecticides are also useful as one of the components of the present method. Preferred organophophate insecticides include acephate (CAS RN 30560-19-1), chlorpyrifos (CAS RN 2921-88-2), chlorpyrifos-methyl (CAS RN 5598-13-0), diazinon (CAS RN 333-41-5), fenamiphos (CAS RN 22224-92-6), and malathion (CAS RN 121-75-5).

In addition, carbamate insecticides are useful in the subject method. Preferred carbamate insecticides are aldicarb (CAS RN 116-06-3), carbaryl (CAS RN 63-25-2), carbofuran (CAS RN 1563-66-2), oxamyl (CAS RN 23135-22-0) and thiodicarb (CAS RN 59669-26-0).

Fungicides that are useful in the present invention include tebuconazole, simeconazole, fludioxonil, fluquinconazole, difenoconazole, 4,5-dimethyl-N-(2-propenyl)-2-(trimethylsilyl)-3-thiophenecarboxamide (silthiopham), hexaconazole, etaconazole, propiconazole, triticonazole, flutriafol, epoxiconazole, fenbuconazole, bromuconazole, penconazole, imazalil, tetraconazole, flusilazole, metconazole, diniconazole, myclobutanil, triadimenol, bitertanol, pyremethanil, cyprodinil, tridemorph, fenpropimorph, kresoxim-methyl, azoxystrobin, ZEN90160, fenpiclonil, benalaxyl, furalaxyl, metalaxyl, R-metalaxyl, orfurace, oxadixyl, carboxin, prochloraz, trifulmizole, pyrifenox, acibenzolar-S-methyl, chlorothalonil, cymoaxnil, dimethomorph, famoxadone, quinoxyfen, fenpropidine, spiroxamine, triazoxide, BAS50001F, hymexazole, pencycuron, fenamidone, guazatine, and cyproconazole.

When a pesticide is described herein, it is to be understood that the description is intended to include salt forms of the pesticide as well as any isomeric and/or tautomeric form of the pesticide that exhibits the same activity as the form of the pesticide that is described.

The pesticides that are useful in the present method can be of any grade or purity that pass in the trade as such pesticide. Other materials that accompany the pesticides in commercial preparations as impurities can be tolerated in the subject methods and compositions, as long as such other materials do not destabilize the composition or significantly reduce or destroy the activity of any of the pesticide components against a target pest(s). One of ordinary skill in the art of the production of pesticides can readily identify those impurities that can be tolerated and those that cannot.

The agricultural actives that are useful in the present invention can be provided in solid or liquid form, and can be provided as emulsions, dispersions, solutions, or in particulate form. The actives can be alone or can be in combination with other materials, as long as such other materials do not destabilize, or significantly reduce or destroy the activity of the active.

The present method can be applied to seeds that have already been treated by others, such as commercially available treated seeds, but the novel method can also include the step of treating seeds with an active. When treatment of a seed with an active is included in the present method, it is preferred that the treatment is carried out so that an evenly distributed coating of the pesticide is applied to the outer surface of the seed without loss of pesticide due to excess liquid falling off of the seed during or after the treatment. After addition of the active, the seeds must not be dried and agitated so long that the active is abraded off the seed due to dusting and scuffing.

The amount of active that is applied to the seed can be any amount, but is preferably between about 0.5 gm of active ingredient/100 kg of seed and about 1,000 gm/100 kg of seed; more preferably between about 25 gm and about 600 gm/100 kg of seed, and even more preferably between about 50 gm and about 400 gm/100 kg of seed.

The active can be applied to the seed in any form and such forms as capsule suspensions (CS), emulsifiable concentrates (EC), emulsions in oil or water (EO and EW), granules (GR), suspension concentrates (SC), soluble granules (SG), soluble concentrates (SL), soluble powders (SP), and water dispersible granules (WG) are suitable. It is preferred to apply the active to the seed in the form of a flowable liquid. The active can be in a true solution in the liquid, or it can be present as small droplets or particles to form a suspension, dispersion or emulsion. Since many pesticides have low water solubility, it is preferred that when water is the liquid, an aqueous dispersion, suspension, or emulsion of the pesticide be used, and that the pesticide be present in the dispersion, suspension, or emulsion in the form of small particles or droplets. As used herein, the term "suspension" will be considered to include any form of liquid containing small particles, and to include the terms dispersion and emulsion.

The particles of pesticide in the liquid suspension can be of any size that permits the suspension to be applied to the seed by any means, such as, for example, by spraying. It is preferred that the particles of pesticide in the suspension have a number average nominal size of less than about 10 microns, more preferably of less than about 5 microns, even more preferably of less than about 2 microns, and even more preferably of less than about 1 micron (be "sub-micron" in size). It is believed that the use of such small particles causes the pesticide to form a more stable and homogenous suspension—thereby allowing a more even distribution of the pesticide over the surface of the seed, and that the small particles are less subject to abrasion from the treated seed after the pesticide treatment has been applied.

The active can be applied to the seed in any type of conventional seed treatment or coating equipment. Application in a seed treating machine having the characteristics of a CMS seed coating machine (Vector Corporation, Marion, Iowa), for example, has been found to be suitable. One method that has been found to be successful for applying a pesticide, such as imidacloprid, to seed, is to mill the imidacloprid to 1-2 micron, or to sub-micron, size and then to add the small particles of imidacloprid to water to form an aqueous suspension. A mill that is capable of reducing solids to fine particles, such as a Mirco-Jet Pulverizer air mill, available from Fluid Energy Processing and Equipment Company, Hatfield, Pa., can be used for the size reduction.

The concentration of the pesticide in the suspension should be low enough to permit easy handling and application of the suspension to the seed—such as by spraying—and thorough distribution of the pesticide among the seeds so that the outer surface of each seed is substantially covered. However, the concentration should be high enough that, when used in combination with the other parameters of seed treatment, to avoid the loss of pesticide from the seeds by dripping or pooling of the treating liquid suspension. Pesticide concentrations of between about 0.1% and about 50%, by weight, are useful for such suspensions, preferred are concentrations between about 0.5% and 15%, by weight, even more preferred are concentrations between about 0.6% and about 5%, and yet more preferred are concentrations of the pesticide between about 1% and 3%, by weight of the suspension. Sticking agents and dyes can also be added to the pesticide suspension to promote the adherence of the suspension to the seeds and to identify the seeds as having been treated.

A desired amount of the suspension of the pesticide is sprayed onto the seed in, for example, a CMS seed treater, over a period of time that is long enough to permit thorough distribution of the suspension over the seed, but short enough so that the treated seed do not completely dry. It is believed that if the treated seed are allowed to remain in a heated seed treater until the suspension is completely dry, the danger of loss of the pesticide by abrasion increases. When the exit temperature of the heated air circulating through the CMS machine is held to about 95° F., and the aqueous suspension contains about 1.6% by weight imidacloprid and 8% by weight of a sticking agent, an application time of between about 3 minutes and about 20 minutes is suitable, and an application time of between about 5 and about 15 minutes is preferred.

After an agricultural active has been applied to the seed, the novel coating can be applied. It is preferred that the polymer of the subject coating be applied to the seed in the form of a film of a liquid suspension, dispersion or emulsion. As used herein, when describing the coating the term "emulsion" will be understood to include all suspensions, dispersions and emulsions. When the liquid in which the active is distributed is water, the emulsion can be termed a latex. It will be understood that when the term "film" is used in this specification, it generally applies to the film of the polymer emulsion in liquid form after application to the seed, unless the context suggests otherwise. Likewise, the term "coating" applies to the coating on the seed that is formed from the curing of the film. When a film containing the active is applied to the seed, it is preferred that the film substantially covers the surface of the seed. However, while preferable, such substantial coverage is not required in order to obtain the advantages of the invention.

The liquid in which the active is suspended is one in which both the active and the polymer have low solubility. When it is said that the active has low solubility in the liquid, it is meant that the solubility of the active in the liquid at 20° C. is less than about 10 g/l. It is preferred that the solubility of the active in the liquid at 20° C. is less than about 1,000 mg/l, a solubility of less than about 200 mg/l is more preferred, less than about 100 mg/l is even more preferred, and less than about 50 mg/l is even more preferred.

When it is said that the polymer has low solubility in the liquid, it is meant that the solubility of the polymer in the liquid at 25° C. is less than about 5%, by weight. It is preferred that the solubility of the polymer is less than about 2%, by weight, less than about 1%, by weight is more preferred, and less than about 0.1%, by weight, is even more preferred.

It is believed that the use of a liquid in which both the polymer and the agricultural active have low solubility provides an advantage to the novel method. By way of example, when the liquid is water, the polymer forms a latex when distributed in the water. A film of the latex is applied to the treated seed, and the latex film has both hydrophobic and hydrophilic character. Without wishing to be bound to this or any other theory, it is believed that this characteristic advantageously modulates the distribution of the active ingredient throughout the coating during drying and formation of the polymer coating. Because the active ingredient has low solubility in the liquid of the film, it is believed that the latex permits the transfer of only a small fraction of the active ingredient into the polymer portion of the latex coating while it is still in the emulsion, but prevents the loss of the active into the liquid. This is believed to prevent the loss of active from the surface of the seed and to retain the major portion of the active on the seed's surface and away from the interface of the coating with the surrounding environment. It is believed that these properties provide the desirable retardation of release rate of the active from the coated, treated seed after the coating has formed, while providing a coating with a low level of active on the outside surface.

Although a water-based emulsion is preferred, emulsions or dispersions of the polymers of the present method in non-aqueous solvents, or in aqueous/non-aqueous solvent mixtures are also within the scope of the invention.

The polymer is added to the liquid under conditions that an emulsion is formed. This can be done by the addition of finely milled particles of the active to the liquid, or a liquid/active mixture can be subjected to high shear to form the emulsion. Such emulsion-forming techniques are well-known in the art.

The polymer can be added to the liquid in any amount, but the concentration of the polymer in the emulsion that is used to form the film should be low enough to permit easy handling and application of the emulsion to the seed—such as by spraying—and thorough distribution of the film among the seeds so that the outer surface of each seed is substantially covered. However, the concentration should be high enough, when used in combination with the other parameters of seed treatment, to avoid the loss of polymer from the seeds by dripping or pooling of the emulsion. It is preferred that the concentration of polymer in the emulsion at the time that a film of the emulsion is applied to the seeds is about 0.5% to about 50%, by weight, more preferred is a concentration of about 0.5% to about 20%, by weight, even more preferred is a concentration of about 2% to about 20%, yet more preferred is a concentration of about 4% to about 15%, by weight, and even more preferred is a concentration of about 5% to about 11%, by weight.

If it is desirable, materials other than the polymer can be added to the liquid in order to serve as plasticizers, emulsifiers, stabilizers, anti-oxidants, fillers, dyes, safeners, and the like. Such materials are well known in the art.

The polymer emulsion can be applied to the seeds in the same type of seed treatment equipment as used for the application of the active ingredient to the seeds. In fact, it is preferred that the emulsion be added to the seeds immediately after the addition of the active ingredient and without removing the seeds from the treater. It is preferred that a short amount of time—on the order of 30 sec. to 3 minutes—elapse between the end of the application of the active and the beginning of the application of the emulsion film. This permits some degree of liquid removal from the treated seeds, but is not long enough to allow the treated seeds to become completely dry.

The amount of the polymer emulsion that is added to the seeds is an amount that is sufficient to provide a coating of the desired thickness. The ratio of the weight of the film of the emulsion that is present on each seed after the emulsion has been added relative to the weight of the treated seed is preferably within a range of from about 1:10 to about 1:50, more preferred is a ratio of about 1:15 to about 1:25, even more preferred is a ratio within a range of about 1:16 to about 1:22, and yet more preferred that the ratio be within a range of about 1:18 to about 1:21.

Without being bound by this or any other theory, it is believed that the combination of the amount of the polymer film that is added to the seed, the concentration of the polymer in the emulsion, and the time required for the addition of the emulsion to the seed is important to provide an overcoat that retains substantially all of the active ingredient on the seed and provides an exterior surface that has a very low concentration of the active ingredient.

After the film of the polymer emulsion has been applied to the seed, it is cured to form the polymer coating. When it is said that the film is "cured", or when "curing the film" is referred to, what is meant is that a solid coating of the polymer is formed from the polymer in the film. Curing is often the result of drying of the liquid from the film, but can also be carried out by chemical reaction, adsorption, sequestration, or other forms of polymer curing that are known in the art.

The subject coating is insoluble in water, as described above, and is present on at least some part of the outer surface of each seed. It is preferred that the coating completely cover the outer surface of each seed. Although the ratio of the weight of the coating relative to the weight of the treated seed can vary over a wide range, it is preferred that the ratio be within a range of from about 1:1 to about 1:1,000, more preferably within a range of about 1:10 to about 1:600, and even more preferably within a range of about 1:20 to about 1:400.

It is believed that the present coating contains some of the active ingredient distributed throughout its thickness. However, because the preferred method of applying the coating is to apply a film of a controlled amount of the particular emulsion to the surface of each seed (rather than to immerse the seed in a large amount of polymer) it is believed that only a small portion of the active on the seed diffuses from the surface of the seed into the coating during the time the film dries and forms a solid coating. It is believed that the concentration of the active in the coating is highest at or near the surface of the seed and decreases to a low level at the interface of the coating with the surrounding environment (the outer surface of the coating).

Although the coating is substantially water insoluble, it must not totally prevent the seed from imbibing water in order to germinate. Therefore, the coating must be sufficiently permeable to water so that the seed can imbibe moisture for germination, but still must retard the release of the active. Moreover, the coating must be sufficiently permeable to oxygen and carbon dioxide so that the normal respiration of the seed is not significantly impaired.

Seeds that have been treated by the subject method can be stored, handled and planted like any other seeds. Similar methods and conditions can be used as are used with any other treated, or non-treated seeds and the same handling and planting equipment can be used that is used for conventional seeds.

Although the subject coating reduces the exposure of persons handling the treated and coated seed to the active, suitable precautions to protect such personnel should be taken.

The following examples describe preferred embodiments within the scope of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

Example 1

This illustrates the treatment of corn seed with imidacloprid.

A coating suspension was prepared by mixing water (133.6 g) at room temperature, with Vinamul 18132 (8.4 g, available from Vinamul Limited Inc.), Seedkare Luster Kote.Plus Red (7.03 g, available from Sub-Sahara Co.), and imidacloprid (2.47 g, available from the Gustafson Company). Prior to preparing the suspension, the size of the imidacloprid particles was reduced from over 100 microns to a nominal average size of approximately 1-2 microns. The size reduction can be carried out by milling for a time sufficient to produce imidacloprid particles having a nominal size of below about 1-2 microns.

The ingredients were then mixed together and the mixture was stirred with a mechanical stirrer at medium speed at room temperature for 20 minutes. At this time the coating suspension was ready for application to the seed.

Corn seed (908.21 g, Asgrow RX601, Lot LF OZ34982, available from Asgrow Seed Company, L.L.C.) was preheated with agitation in the drum of a CMS seed treatment machine (model PSC-0.5; available from Vector Corporation, Marion, Iowa) for three minutes at one-half rotation of the drum every minute. The inlet and exhaust temperatures of the air flowing into and out of the CMS machine were set to be controlled at 101° F. and 90° F. respectively. The actual exhaust temperature was 99° F. The drum speed was set at 20 rpm and the drum position angle was down. Atomizing air flow rate for spray application of the coating suspension was 50 cfh and the tube size on the pump was 16. The pump speed was set at 5.5. Over a period of 14.5 minutes, the coating suspension was sprayed directly on the seed through a nozzle. A pulse spray mode was used. The weight of the seed after application of the coating suspension was 921.94

Example 2

This illustrates the treatment of corn seed with imidacloprid and subsequent coating with a polymer latex having a glass transition temperature of 15° C.

Corn seed (908.13 g) was treated with a coating suspension that contained water (133.6 g), imidacloprid (2.48 g; milled as described in Example 1), Vinamul 18132 (8.39 g), and Seedkare Lusterkote Plus Red (7.03 g). The coating suspension was prepared and applied to corn seed as described in Comparative Example 1, except that the time to apply the suspension was about 8 minutes.

After the coating suspension had been applied to the corn seed, and while the treated seed was still in the drum of the CMS machine, an aqueous emulsion of a polymer latex was applied to the seed. The polymer latex emulsion was prepared by mixing water (38.1 g) at room temperature, with polymer latex (11.7 g, NMS-7 polymer latex having a solids content of 45.8% by weight; and having a glass transition temperature ($T_g$) of 15° C., available from the Stepan Company, Northfield, Ill.). The conditions for the CMS Treater during the overcoating process were as follows: the inlet temperature was set for 106° F.; exhaust temperature (set) 90° F.; exhaust temperature (actual) 99° F.; seed temperature during overcoating was 34.2° F.; drum speed 20 rpm, drum angle was down, atomizing air pressure was 50 psi; tube size on the pump was 16; pump speed was 5; and time to apply the overcoating emulsion was 2 min. 45 sec. The weight of the seed after treating and overcoating was 929.49 g.

Example 3

This illustrates the treatment of corn seed with imidacloprid and subsequent coating with a polymer latex having a glass transition temperature of 25° C.

Corn seed (908.24 g) was treated with a coating suspension that contained water (133.6 g), imidacloprid (2.47 g), Vinamul 18132 (8.39 g), and Seedkare Lusterkote Plus Red (7.02 g). The coating suspension was prepared and applied to corn seed as described in Example 2.

After the coating suspension had been applied to the corn seed, an aqueous emulsion of a polymer latex was applied to the seed as described in Example 2. The polymer latex emulsion was prepared by mixing water (33.1 g) at room temperature, with polymer latex (12.7 g, NMS-7 polymer latex having a solids content of 39.6% by weight; and having a glass transition temperature ($T_g$) of 25° C., available from the Stepan Company, Northfield, Ill.). The conditions for the CMS Treater during the overcoating process were the same as in Example 2, and the time to apply the overcoating emulsion was 3 min. 10 sec. The weight of the seed after treating and overcoating was 929.31 g.

Example 4

This illustrates the treatment of corn seed with imidacloprid and subsequent coating with an aqueous dispersion of ethylcellulose.

Corn seed (908.14 g) was treated with a coating suspension that contained water (133.6 g), imidacloprid (2.47 g), Vinamul 18132 (8.38 g), and Seedkare Lusterkote Plus Red (7.02 g). The coating suspension was prepared and applied to corn seed as described in Example 2.

After the coating suspension had been applied to the corn seed, an aqueous dispersion of ethylcellulose was applied to the seed as described in Example 2. The ethylcellulose dispersion was prepared by mixing water (30 g) at room temperature, with ethylcellulose (20.16 g, Surelease polymer, Lot E-7-19010; an off-white, turbid, liquid dispersion having a solids content of 24%-26% of ethylcellulose 20 cP, and also containing ammonium hydroxide, medium chain triglycerides and oleic acid in small amounts; available from Colorcon Company). The conditions for the CMS Treater during the overcoating process were the same as in Example 2, and the time to apply the overcoating emulsion was 3 min. 30 sec. The weight of the seed after treating and overcoating was 929.07 g.

Example 5

This illustrates the treatment of corn seed with imidacloprid and subsequent coating Aquacoat Type ECD formulation of ethylcellulose.

Corn seed (908.48 g) was treated with a coating suspension that contained water (133.6 g), imidacloprid (2.47 g), Vinamul 18132 (8.38 g), and Seedkare Lusterkote Plus Red (7.05 g). The coating suspension was prepared and applied to corn seed as described in Example 2.

After the coating suspension had been applied to the corn seed, Aquacoat Type ECD-30 aqueous dispersion of ethylcellulose (ECD) was applied to the seed as described in Example 2. The ECD dispersion was prepared by mixing water (33.2 g) at room temperature, with Aquacoat Type ECD-30 (16.8 g of a while liquid dispersion having 27% by weight of ethylcellulose; the dispersion having a total solids content of 30%, and containing cetyl alcohol and sodium lauryl sulfate. Available from FMC Corporation). The conditions for the CMS Treater during the overcoating process were the same as in Example 2, and the time to apply the overcoating emulsion was 3 min. 40 sec. The weight of the seed after treating and overcoating was 927.7 g.

Example 6

This illustrates the treatment of corn seed with imidacloprid and subsequent coating with a vinyl acetate-ethylene copolymer.

Corn seed (908.14 g) was treated with a coating suspension that contained water (133.6 g), imidacloprid (2.47 g), Vinamul 18132 (8.37 g), and Seedkare Lusterkote Plus Red (7.03 g). The coating suspension was prepared and applied to corn seed as described in Example 2.

After the coating suspension had been applied to the corn seed, an aqueous dispersion of Airflex 500 was applied to the seed as described in Example 2. The Airflex 500 dispersion was prepared by mixing water (45.38 g) at room temperature, with Airflex 500 (4.62 g; Airflex 500 is a fine-particle-size aqueous dispersion of a vinyl acetate-ethylene copolymer; the emulsion is used as a base for interior and exterior paints and other flexible coatings. The solids content of the emulsion is 55% by weight and the average particle size is 0.17 microns. Available from Air Products Company). The conditions for the CMS Treater during the overcoating process were the same as in Example 2, and the time to apply the overcoating emulsion was 5 min. 10 sec. The weight of the seed after treating and overcoating was 924.23 g.

Example 7

This illustrates the release profiles of imidacloprid into water from treated corn seeds with and without polymer overcoating and shows the release-retarding effect of certain polymer overcoats.

The treated corn seed from Examples 1 through 5 was tested for the release rate of imidacloprid into excess water. Treated seeds were placed in an amount of water sufficient that at 100% release of the active from the treated seeds, the total active present in the water is less than approximately one-third the water solubility level of the active. The water containing the seeds is then agitated by shaking. At intervals, an aliquot is taken and filtered to separate the active that is dissolved in the water from the active that remains on the seed, or remains in the form of a controlled release matrix. The filtered aliquot is then assayed for active present. Release curves show the percent of the total active that was originally present on the seeds that has been released into the water as a function of the time of immersion.

In a typical sample, treated seeds containing approximately 45 mg of imidacloprid were placed in a 16 ounce bottle along with 450 ml of water. The total amount of imidacloprid in the bottle was calculated to be about 100 ppm, which is less than one-third of the water solubility limit of imidacloprid at room temperature (about 510 ppm). The bottle containing the water and the seeds was then inverted approximately 100 times and an aliquot of liquid was removed and the time of removal was noted. The bottle was then placed on a platform shaker and agitated until time for the next sample withdrawal. The aliquot was filtered with a 0.45 micron PTFE filter and the filtered aliquot was assayed for imidacloprid content by HPLC. An Alltech Alltime C18 reverse phase column (5 micron particle size with column dimensions of 250×4.5 mm) was used with a flow rate of 1.2 ml/min and an injection volume of 20 microliters. The mobile phase contained 30% of acetonitrile and 70% of water. The UV detector (Varian 9050) was set at 220 nm and the retention time for imidacloprid was between 6 and 7 min. For subsequent time points of the release curve, the procedure described above was used to determine the concentration of active in the water.

When seeds were treated with, for example, tebuconazole, the same procedure was used to determine the release rate, except that the relative amounts of treated seeds and water were adjusted to maintain the maximum level of the active at less than one-third of its solubility level.

Figure 1:
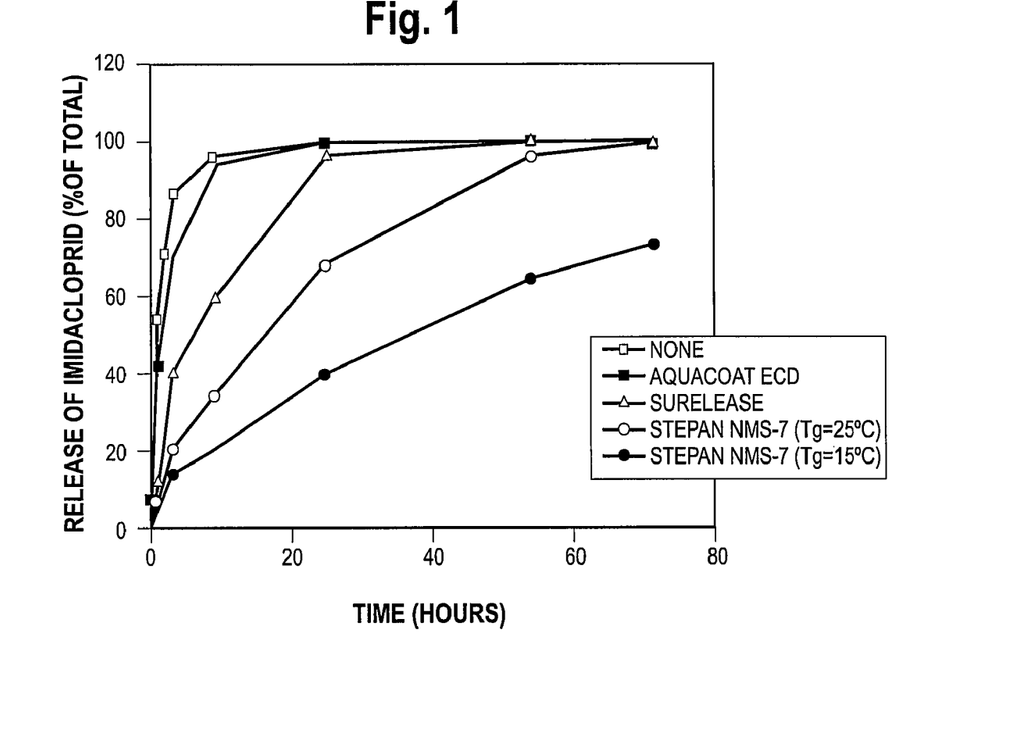
FIG. 1 shows the release of imidacloprid as a function of time from corn seed that had been treated with imidacloprid followed by no overcoating, or overcoating according to an embodiment of the subject method with an emulsion containing Aquacoat ECD, Surelease Polymer, Stepan NMS Latex with $T_g = 25°$ C., or Stepan NMS Latex with $T_g = 15°$ C.

The results of the release rate test are shown in FIG. 1, where the percent release of the total imidacloprid on the seed is shown as a function of time for each of the treated and coated seeds and for the treated and uncoated seed. It can be seen that imidacloprid was lost from the uncoated seed more rapidly that for any of the seeds having a polymer coating. However, the release rate varied significantly according to the type of polymer and the glass transition temperature of the polymer. Seeds treated with the two Stepan NMS-7 latex polymers provided the highest reduction in release rate, and showed that the release rate could be varied by varying the glass transition temperature of the polymer coating. In this instance, it was seen that the polymer having the lower $T_g$ provided the lower release rate. However, it is believed that the effect of $T_g$ upon release rate may be reversed for polymers having different structures. It is believed that this shows that with a given polymer, the release rate of the active can be controlled by selecting a polymer having a $T_g$ that will provide the desired rate.

Example 8

This illustrates the treatment of cotton seed with imidacloprid and shows the effect on imidacloprid release rate of overcoating the treated cotton seed with a polymer coating derived from an aqueous latex.

Cotton seed (908 g, which had been received from Deltapine Company (Bollgard cotton seed with Roundup Ready® technology; Lot#458 BR-S-9299-2, treatment code 2) was treated with a coating suspension that contained water (133.6 g), Vinamul 18132 (8.46 g), Seedkare Lusterkote Plus Red (7.04 g) and imidacloprid (2.47 g). The coating suspension was prepared and applied to the seed in the manner described in Example 2, except that cotton seed was substituted for corn seed.

After the seed was treated with the imidacloprid suspension, a portion of the treated seed were removed from the CMS machine and the remainder of the seed were left in the machine. An aqueous emulsion of a polymer latex (12.7 g of NMS-7, polymer latex, having a $T_g$ of 25° C., available from Stepan Company, diluted with 38.1 g of water) was applied to the seed as described in Example 2.

Samples of the treated cotton seed with and without the polymer overcoating were tested by the same technique as described in Example 7 to determine the release profiles of imidacloprid into excess water.

Figure 2:
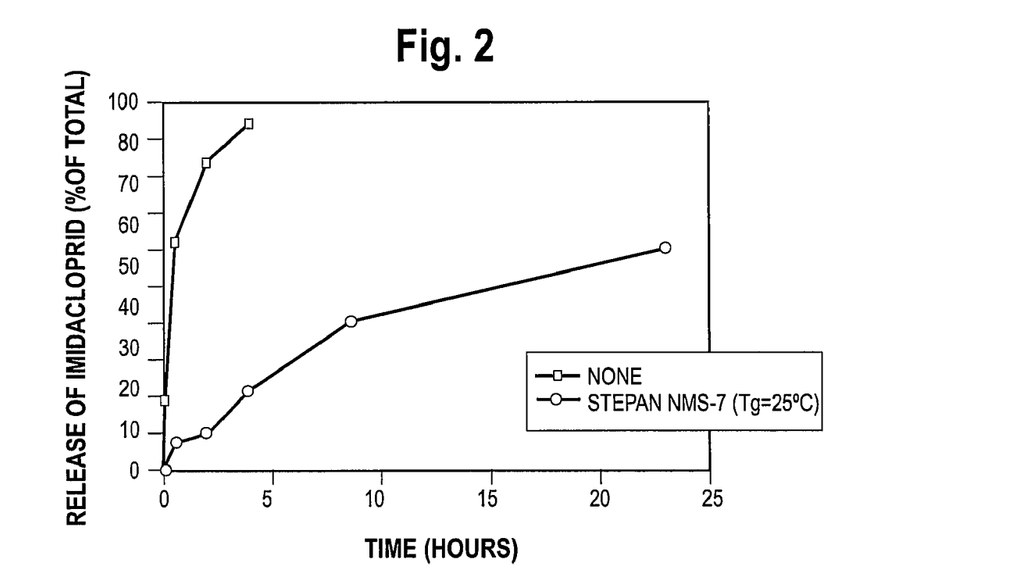
FIG. 2 shows the release of imidacloprid as a function of time from cotton seed that had been treated with imidacloprid followed by no overcoating, or overcoating according to an embodiment of the subject method with an emulsion containing Stepan NMS Latex.

The release profiles of imidacloprid from treated cotton seed with and without the novel coating are shown in FIG. 2. It can be seen that the uncoated seeds lost over 90%, by weight, of the imidacloprid that had been deposited on the treated seeds within 5 hours. However, cotton seeds having the coating lost only 30% or less in the same time. This showed that the novel coating could be applied to treated cotton seed as well as to corn seed, and that the coating provided the same advantageous retardation of release rate of the imidacloprid as shown for coatings applied to corn.

Example 9

This illustrates the effect of overcoating corn seed treated with tebuconazole with polymers having different glass transition temperatures.

Three separate batches of corn seed (908 g) were treated in a CMS seed treater with tebuconazole (supplied as RAXIL® in a liquid mixture containing 6% by weight tebuconazole, RAXIL® is available from Bayer Corporation). A suspension of RAXIL® (15.2 ml) was prepared by mixing it with Vinamul 18132 (8.32 g) and Seedkare Lusterkote Plus Red (7.0 g) in water (133.6 g). The suspension was applied to corn seed by the methods described in Example 2.

One batch of the corn seed treated with tebuconazole was left without further treatment.

For the other two batches of treated corn seed, after the tebuconazole coating suspension had been applied to the seed, a polymer latex emulsion was applied by the methods described in Example 2. One batch was coated with a latex emulsion prepared by mixing water (38.1 g) at room temperature with polymer latex (11.1 g of Stepan NMS-7 polymer latex having a solids content of 45.8% by weight, and having a $T_g$=15° C., available from Stepan Co., Northfield, Ill.). The emulsion was applied to the seeds within a period of 4 min. 20 sec. The weight of the treated and overcoated seeds was 933.1 g.

The final batch of tebuconazole treated corn seed was overcoated as described above, except with a latex emulsion prepared by mixing water (33.1 g) at room temperature with polymer latex (12.7 g of Stepan NMS-7 polymer latex having a solids content of 39.6% by weight, and having a $T_g$=25° C., available from Stepan Co., Northfield, Ill.). The emulsion was applied to the seeds within a period of 4 min. 50 sec. The weight of the treated and overcoated seeds was 931.58 g.

Figure 3:
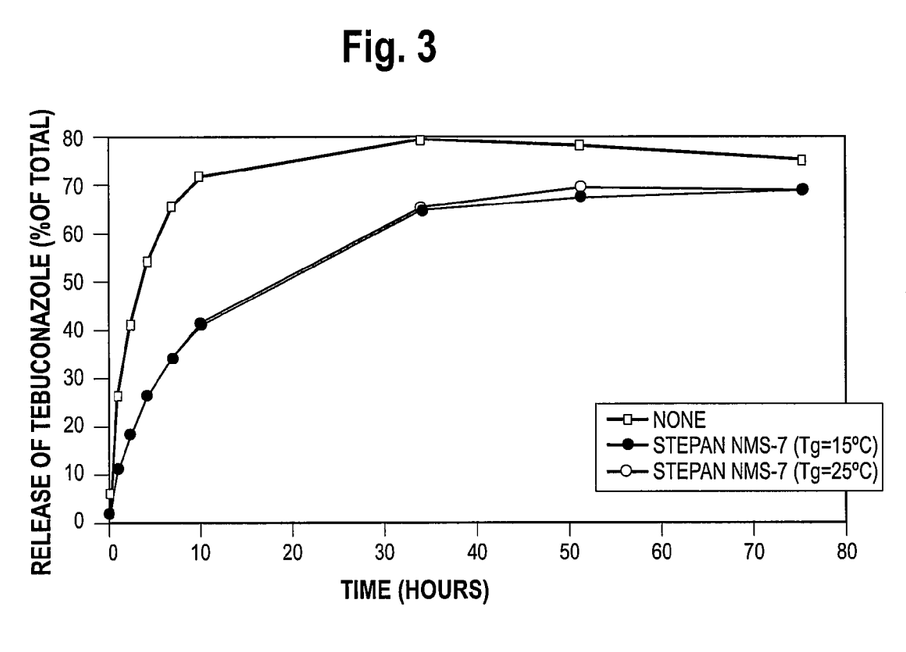
FIG. 3 shows the release of tebuconazole as a function of time from corn seed that had been treated with tebuconazole followed by no overcoating, or overcoating according to an embodiment of the subject method with an emulsion containing Stepan NMS Latex with $T_g = 15°$ C., or Stepan NMS Latex with $T_g = 25°$ C.

The release rate of tebuconazole from the three batches of treated corn seed was determined as described in Example 7, except that the assay was for tebuconazole rather than imidacloprid. The release rate profiles for tebuconazole into water are shown in FIG. 3 and indicate that coating with either polymer provides a controlled rate of release of the tebuconazole relative to the seeds having no overcoating. Little difference in the release rate was noticed as a function of the $T_g$ of the polymers in this test.

All references cited in this specification, including without limitation all papers, publications, presentations, texts, reports, manuscripts, brochures, internet postings, journal articles, periodicals, and the like, are hereby incorporated by reference. The citation and/or discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method of controlling the release rate of an agricultural active ingredient from a seed treated with the active ingredient, the method comprising the steps of:
   providing a seed that has been treated with an agricultural active ingredient;
   applying to the treated seed, at a temperature of about 34° F. (about 1° C.), an aqueous emulsion of a polymer latex, wherein the polymer latex has a solubility in water at 25° C. of less than 5% by weight, a glass transition temperature of about 15° C. to about 40° C. and wherein the active ingredient has a solubility in water at 20° C. of less than 10 g/L; and
   curing the polymer latex emulsion to form a water insoluble, non-migrating polymer coating on the surface of the treated seed, wherein the polymer coating that is formed from the polymer latex emulsion has a glass transition temperature within the range of from about 15° C. to about 40° C., thereby providing a coating which retards the release rate of the agricultural active ingredient from the seed.

2. The method according to claim 1, wherein the ratio of the weight of the coating to the weight of the treated seed is from about 1:1 to about 1:1,000.

3. The method according to claim 1, wherein the ratio of the weight of the coating to the weight of the treated seed is from about 1:10 to about 1:600.

4. The method according to claim 1, wherein the ratio of the weight of the film to the weight of the treated seed is from about 1:20 to about 1:400.

5. The method according to claim 1, wherein the agricultural active ingredient is a pesticide.

6. The method according to claim 5, wherein the pesticide is selected from the group consisting of herbicides, insecticides, acaracides, fungicides, nematocides, and bactericides.

7. The method according to claim 1, wherein the seed is the seed of a plant selected from the group consisting of corn, peanut, canola/rapeseed, soybean, curcubits, cotton, rice, sorghum, sugar beet, wheat, barley, rye, sunflower, tomato, sugarcane, tobacco, oats, vegetables, and leaf crops.

8. The method of claim 1, wherein the polymer latex has a glass transition temperature of 15° C.

9. The method of claim 1, wherein the polymer latex has a glass transition temperature of 25° C.

\* \* \* \* \*